United States Patent [19]

Glenn

[11] Patent Number: 5,056,721
[45] Date of Patent: Oct. 15, 1991

[54] METHOD FOR CLASSIFYING WHEAT KERNELS AS HARD OR SOFT

[75] Inventor: Gregory M. Glenn, Vallejo, Calif.

[73] Assignee: The United States of America as represented by the Secretary of Agriculture, Washington, D.C.

[21] Appl. No.: 536,865

[22] Filed: Jun. 12, 1990

[51] Int. Cl.$^5$ .............................................. B02B 5/00
[52] U.S. Cl. ........................................... 241/9; 73/78; 209/699; 241/24
[58] Field of Search .................... 241/6, 9, 24; 73/78, 73/81; 209/699; 83/870, 871, 872

[56] References Cited

U.S. PATENT DOCUMENTS 4,703,647 11/1987 Eckhoff et al. ...................... 241/6 X
4,807,465 2/1989 Botzolakis et al. ...................... 73/78

OTHER PUBLICATIONS

Katz et al., "A New Grain Hardness Tester," *Cereal Chemistry*, 36: 393-401 (1959).
P. J. Mattern, "Wheat Hardness: A Microscopic Classification of Individual Grains," *Cereal Chemistry*, 65: 312-315 (1988).
Lai et al., "Determination of Hardness in Wheat Mixtures. II. Apparatus for Automated Measurement of Hardness of Single Kernels," *Cereal Chemistry*, 62: 178-184 (1985).
Y. Pomeranz et al., "Wheat Hardness Determined by a Single Kernel Compression Instrument with Semiautomated Feeder," *Cereal Chemistry*, 65: 86-94 (1988).
Eckhoff et al., "A Rapid Single-Kernel Wheat Hardness Tester," *Cereal Chemistry*, 65: 503-508 (1988).

*Primary Examiner*—Mark Rosenbaum
*Assistant Examiner*—Frances Chin
*Attorney, Agent, or Firm*—M. Howard Silverstein; John D. Fado; Margaret A. Connor

[57] ABSTRACT

A sectioning method is described for accurately and objectively classifying individual wheat kernels as hard or soft wheat. A kernel is cut to obtain a section having a thickness in the range of about 1.3 to 4.8 microns; if the section remains intact, the kernel is classified as hard, and if the section does not remain intact, the kernel is classified as soft. The method finds particular use for detection of lots of wheat where hard and soft varieties have been intermixed and for classifying breeding selections.

4 Claims, 1 Drawing Sheet

METHOD FOR CLASSIFYING WHEAT KERNELS AS HARD OR SOFT

BACKGROUND OF THE INVENTION

1. Field of the Invention

The invention relates to classification of wheat varieties as hard or soft wheats. In particular, it relates to a sectioning method for classifying individual wheat kernels as hard or soft.

2. Background Art

Wheat is a major food crop worldwide and is used to produce a wide diversity of baked food products. Wheat varieties are often broadly classified as "hard" or "soft," although other subclasses do exist. Although no definition for the term wheat "hardness" has been universally accepted, this property is important for predicting milling properties and end-uses of wheat varieties. Wheat varieties of similar genetic makeup tend to be suitable for specific products. Hard wheat varieties generally have a harder texture than soft wheats and are genetically different from soft wheats. Hard wheat varieties are used primarily for leavened bread products. For example, bread flour is usually made from hard wheat, largely because of its relatively high protein content and desirable gluten quality. The actual hardness of the wheat is in itself of some significance, however, since hard wheat varieties yield flour of a granular character considered desirable in breadmaking. Hard wheats include hard red winter, hard red spring, and durum. "Soft" flours from soft wheat varieties are preferred for cake and pastry products. Soft wheats include soft red winter, soft white winter, and club. Wheat shipments that contain a mixture of hard and soft wheat varieties are not suitable for either breads or pastries and are either discounted at the marketplace or sold for livestock feed. Therefore, a classification system based on genetic similarities was developed for marketing wheat. Until recently, hard and soft wheat classes were accurately classified by Federal Grain Inspectors using visual methods based on distinct physical characteristics. This is because hard and soft wheats were maintained by breeding programs which preserved the kernel morphology of wheats generally recognized as hard or soft. However, new wheat cultivars have not maintained distinct visual characteristics and are difficult to classify by appearance. Thus, there is a need for an accurate, objective method for classifying wheat kernels to detect lots of wheat where hard and soft varieties have been intermixed along the marketing route. Also, a rapid, accurate method is needed by breeders to classify breeding selections.

Methods which classify hard and soft wheats by means other than physical appearance have been developed. Near infrared reflectance (NIR) spectroscopy which measures wheat hardness based on the scattering of near infrared radiation by ground wheat is becoming the industry standard for differentiating hard and soft wheat samples (AACC Method 39–70, *Approved Methods of the American Association of Cereal Chemists* (AACC), 8th ed., The Association, St. Paul, Minn. (1983)). However, this and many other methods used for classifying hard and soft wheat varieties use bulk amounts of a wheat sample. Bulk readings give an average value from which to classify a wheat sample. Thus, mixed shipments of wheat that contain mostly hard wheat would still be classified as hard. A single grain method of classifying hard and soft wheats is needed to detect shipments of wheat that have been mixed.

Very few single-grain methods of classifying wheats have been developed. Methods that classify wheat kernels by measuring a physical property of the wheat kernel include measurement of mechanical resistence to penetration (indentation), crushing, or shearing. Katz et al. (*Cereal Chemistry* 36: 393–401 (1959)) described an indentor which assesses the hardness of individual wheat kernels based on penetration of a spring-loaded stylus into a transverse wheat kernel section prepared with a freezing microtome. Significant variations in hardness within a kernel section were found. The technique was never tested as a means for classifying hard and soft wheat varieties. P. J. Mattern (*Cereal Chemistry* 65: 312–315 (1988)) described a microscopic method for identification of wheat hardness in single wheat kernels. In this method, wheat kernels are crushed with corrugated rollers and rated from 1 to 10 (soft to hard) on a hardness index established by the researcher, based on the physical characteristics of the fracture surfaces when viewed under a dissecting microscope. While the method accurately classifies hard and soft wheat grains, the technique is labor intensive and not adaptable to automation. Lai et al. (*Cereal Chemistry* 62: 178–184 (1985)) developed a continuous automatic single-kernel hardness tester which records compression forces (stress) encountered when crushing a wheat kernel as a function of time (strain). A sampling rate of 15 kernels per minute was achieved with this system at a reported accuracy of 90%. It is pointed out by the researchers (see Y. Pomeranz et al., *Cereal Chemistry* 65: 86–94 (1988)) that with this method, variation in hardness values within a variety may be greater than between varieties. In addition, kernel positioning, degree of kernel shriveling, and kernel geometry affect accuracy. Eckhoff et al. (*Cereal Chemistry* 65: 503–508 (1988)) developed a single kernel wheat hardness tester which differentiates hard wheat from soft by shearing through a raw kernel and recording the associated breakage curves. The peak force, peak sharpness, and transformation of curve data were used to differentiate samples. The method showed 80% classification accuracy for the five hard and five soft varieties tested. The method is affected by variations in kernel moisture content, size, and orientation during shearing.

SUMMARY OF THE INVENTION

The method of the invention provides an accurate, objective method for classifying single kernels of wheat as hard or soft. In the method of the invention, a raw wheat kernel having at least one substantially flat, planar face is cut at a predetermined thickness at which essentially all hard wheat varieties remain intact and essentially all soft wheat varieties do not remain intact.

The invention provides a method for objectively and accurately classifying individual wheat kernels as hard or soft. It is accurate for a wide range of wheat varieties and for kernels having a wide range of moisture levels. Further, kernel shape, size, and degree of shriveling, and orientation of the kernel during cutting do not affect the results of the method as occurs with other methods. The method lends itself to automation.

Surprisingly, I have found that endosperm cohesiveness of a wheat kernel section of a particular thickness accurately classifies hard and soft wheat varieties. Apparently, the cohesiveness of sections from wheat endosperm reflects inherent differences in the mechanical properties of hard and soft kernels. I have found that the differences in cohesiveness were consistent even for samples that were not clearly differentiated or were classified incorrectly by other methods such as percent protein or NIR hardness scores.

The method of the invention is useful for screening commercial lots of wheat to identify those lots where hard and soft wheat varieties have been intermixed. In this aspect, the invention provides a means for quality control of wheat samples.

The invention is also useful to wheat breeders and researchers who need to accurately classify wheat samples. Because only a portion of each kernel is needed for testing, the invention finds particular use in those instances where only limited amounts of sample are available.

In accordance with this discovery, it is an object of the invention to provide means to accurately and objectively classify single kernels of wheat as hard or soft.

A further object of the invention is the provision of a quality control method to monitor wheat samples.

Other objects and advantages of the invention will become readily apparent from the ensuing description.

DETAILED DESCRIPTION OF THE INVENTION

Figure 1:
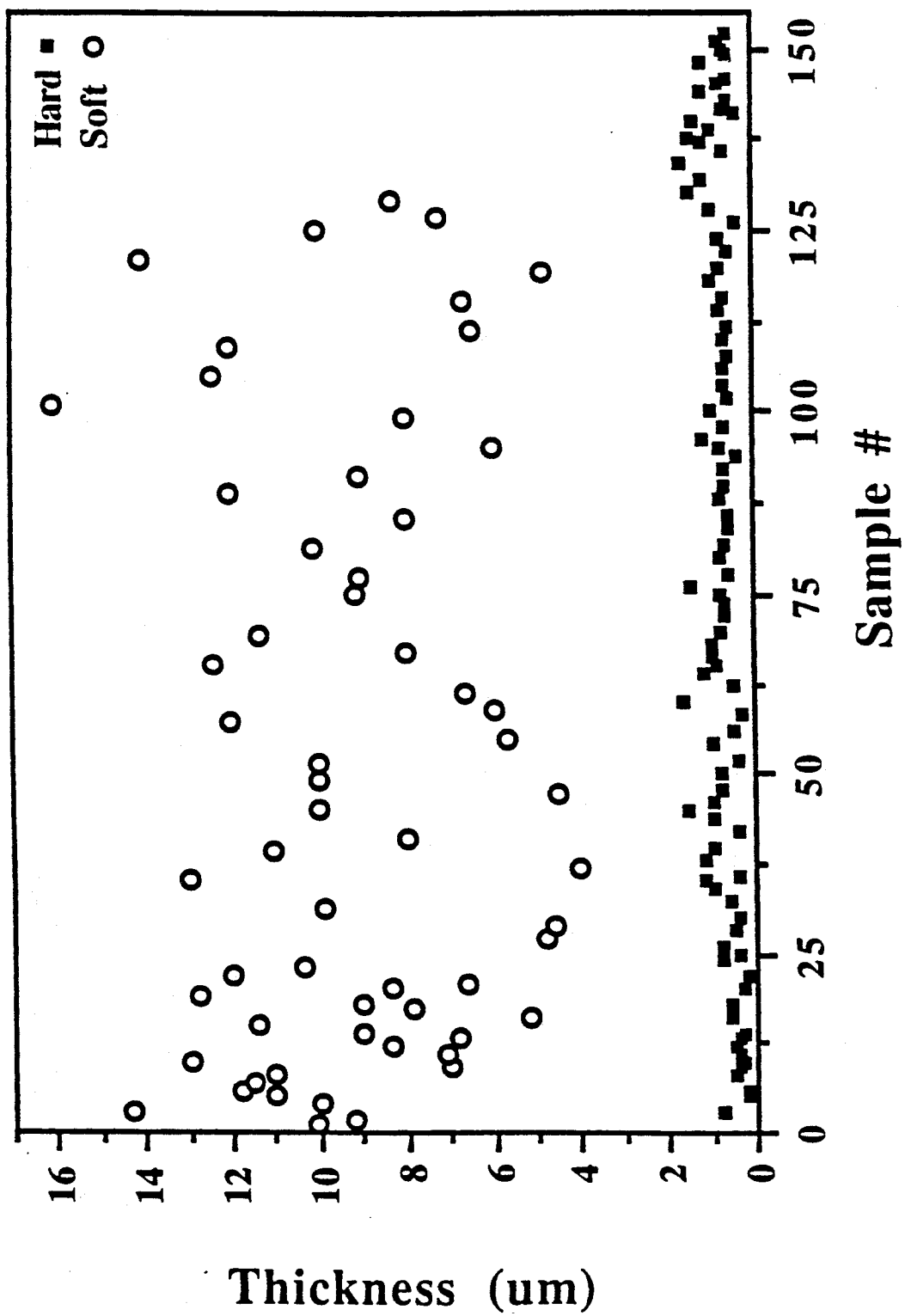
FIG. 1 shows a scatter plot of thickness of intact cross sections of raw wheat kernels for 152 samples representing 60 wheat varieties: 93 samples representing 34 hard wheat varieties and 59 samples representing 26 soft wheat varieties.

In the method of the invention, a wheat kernel is sectioned in accordance with certain critical parameters. If the section remains intact, that is, if it remains whole, it is classified as hard wheat. If the section does not remain intact, that is, if the section crumbles or otherwise breaks into pieces, it is classified as soft wheat.

Prior to sectioning a wheat kernel, the kernel is treated to have at least one substantially flat, planar face, that is, a face that is substantially free of uneven or jagged edges. One convenient way to obtain a substantially flat, planar face on a wheat kernel is to grind or cut the kernel surface with a sharp, cutting instrument such as a rotary knife or microtome. Another convenient method to obtain a substantially flat, planar face is to section a kernel into progressively thinner sections using a sharp, cutting instrument, such as a microtome or knife, until the blade cuts evenly through the kernel. To cut evenly across a kernel in the cutting plane, the kernel is maintained in a rigid position by conventional means known in the art. The orientation of the face is not critical, however, the flat, planar face must be below the subaleurone layer (the single layer of endosperm cells immediately inside of the aleurone layer and which is, morphologically, the outer layer of cells of the endosperm). Generally, a face at least 50 microns below the aleurone layer meets the criterion of being below the subaleurone layer.

Next, the kernel is cut at a predetermined thickness measured from the planar face, and substantially parallel thereto, to obtain a kernel section having a thickness at which essentially all hard wheat varieties remain intact and essentially all soft wheat varieties do not remain intact. I have surprisingly found that there is a critical range of thickness at which a kernel may be cut at which essentially all of the sections prepared from hard wheat varieties remain intact and essentially all of the sections prepared from soft wheat varieties do not remain intact. As shown in FIG. 1, of 152 wheat samples tested representing 60 varieties of hard and soft wheats, intact sections of hard wheat kernels were obtained in the range of 0.2 to 1.6 $\mu$m. The thinnest section at which a soft wheat variety could be cut without breaking up was 4 $\mu$m, and most soft wheat varieties did not remain intact at a thickness of 4.8 $\mu$m. The data illustrating section thicknesses at which essentially all hard wheat varieties remain intact and essentially all soft wheat varieties do not remain intact is presented in Table 1, below.

TABLE 1

| Section Thickness ($\mu$m) | Hard Wheat Sections Intact (%) | Soft Wheat Sections Intact (%) |
| --- | --- | --- |
| 1.3 | 92 | 0 |
| 1.4 | 97 | 0 |
| 1.5 | 98 | 0 |
| 1.6 | 100 | 0 |
| 2.0 | 100 | 0 |
| 2.5 | 100 | 0 |
| 3.0 | 100 | 0 |
| 4.0 | 100 | 1.7 |
| 4.5 | 100 | 3.3 |
| 4.6 | 100 | 5.1 |
| 4.8 | 100 | 8.5 |

As can be seen from the data, essentially all hard wheat varieties remain intact and essentially all soft wheat varieties do not remain intact when cut at a thickness of about 1.3 to 4.8 $\mu$m. For convenience, it is preferable to prepare sections within the range while avoiding the extreme ends of the range, for example, in a range of 1.5 to 4.5 $\mu$m, e.g., at 1.6, 2, 2.5, 3 or 4 $\mu$m. At these thicknesses, hard wheat sections are typically pliable, and cohesive, whereas soft wheat sections typically crumble throughout the entire endosperm structure.

The method accurately classifies wheat kernels over a broad range of moisture content, e.g., 2 to 17%. This is important because wheat kernels from different sources have variable moisture content. Also, as shown in the Example, kernel shape, size, degree of shriveling, and orientation of the kernel during cutting do not affect the results as with many other methods.

The method of the invention is inherently more accurate in classifying hard and soft wheat samples than methods that measure hardness as a function of force placed on a kernel, e.g., to crush, shear, or penetrate the kernel. This is because force measurements may be affected by the kernel geometry, moisture content, and shriveling. As shown in the Example, below, the method of the invention is not influenced by these factors. Furthermore, the method of the invention measures mechanical properties unique to hard or soft wheat endosperm as illustrated by the fact that it correctly classified various hard and soft wheat samples that were misclassified by NIR hardness, a bulk sample method also independent of kernel geometry, shriveling, and moisture content.

The following example is intended only to further illustrate the invention and is not intended to limit the scope of the invention which is defined by the claims.

EXAMPLE

Wheat Samples. Blended samples of commercially grown hard and soft wheat varieties (1987 crop year) were obtained from four USDA regional wheat quality laboratories located in Kansas, Ohio, North Dakota and Washington. Moisture content of the samples was determined by AACC method 44-15A (*Approved Methods of the AACC*, The Association, St. Paul, Minn.). In addition, 41 breeder samples of Foundation Seed, 36 wheat blends from the Federal Grain Inspection Service (FGIS) and 24 samples of Winter/Spring wheat varieties from North Dakota were included in this study. Hardness and protein content of each sample was obtained using near infrared reflectance according to AACC methods 39-70 and 39-11A, respectively.

Sectioning Method. A flat surface was prepared on the germ-end of an individual kernel by removing 2-3 mm of tissue with a metal file. The grains were secured to plastic microtome stubs using a liquid cyanoacrylate adhesive (Krazy Glue Inc., Itasca, Ill.). A portion (1-2 mm) of the brush end of the grain was filed away and the sample was inserted in an ultramicrotome (Sorvall MT-2). Single kernels from 152 different samples were placed in number coded containers and randomized prior to sectioning to conceal their origin. The kernel face was sectioned with a glass knife at a thickness of 8 $\mu m$ until the entire cross-sectional surface of the kernel was in the cutting plane. Section thickness, as determined by the microtome setting, was progressively reduced and recorded when the thinnest possible intact section for each variety was achieved. Effect of moisture content on section thickness was tested for three hard and three soft wheat varieties equilibrated to 2%, 9%, 11%, 14%, and 17% moisture content using humidity chambers containing sulfuric acid solutions.

Analysis. Classificatory discriminant analysis of the data (SAS/STAT, *Guide for Personal Computers*, 6th ed. Cary, NC: SAS Institute Inc. (1985)) was performed on the first observation of each variety in order to calculate a discriminant function. The discriminant function was then used in classifying the remaining data. Due to the unequal variances between wheat classes, a quadratic discriminant analysis was performed on data for thickness and hardness. A linear discriminant function using a pooled variance was used for the protein data since the variances were homogenous between wheat classes. The data were classified into two classes comprised of hard and soft wheats.

Results. The thinnest possible cross-section that remained intact was noted for each sample. FIG. 1 shows a scatterplot of thickness of intact cross section of each sample. The range of values for the hard wheats was from 0.2 to 1.6 $\mu m$. These sections were transparent slices that remained cohesive and pliable when agitated with a camel hair brush. Thick cuts (4-16 $\mu m$) were required in soft wheat varieties to achieve sections that were relatively intact. Section thickness was not significantly affected by moisture content in the range tested (2-17%).

The accuracy of classification of wheat samples using the method of the invention, NIR, and percent protein was compared. The 152 samples tested represented 60 wheat varieties: 93 samples representing 34 commercial hard wheat varieties and 59 samples representing 26 commercial soft wheat varieties. The shape, size and degree of shriveling of the samples varied with kernel variety and environmental growing conditions. Table 2, below, shows the percentage of wheat samples correctly classified based on discriminant functions for thickness (the method of the invention), NIR hardness, and percent protein. As shown in the Table, all of the samples were correctly classified as hard or soft using the method of the invention. Further, the data in Table 2 (100% correct classification) show that variables such as kernel shape, size, and degree of shriveling did not affect the accuracy of the method of the invention.

When wheats were classified by NIR hardness as either hard or soft, four hard wheat samples were misclassified as soft wheat which resulted in a 2.2% error. Protein content was not an accurate parameter for classifying wheat samples. Only 43.3% of the samples were correctly classified into hard and soft wheat classes by protein content.

TABLE 2

| Wheat Class | % of Samples Correctly Classified | | |
|---|---|---|---|
| | Method of the Invention | NIR Hardness | Percent Protein |
| Hard | 100 | 95.7 | 20.4 |
| Soft | 100 | 100 | 66.1 |
| Total | 100 | 97.8 | 43.3 |

The effect of kernel orientation on the accuracy of the method was examined as follows: three hard and three soft wheat varieties were sectioned in accordance with the method of the invention at three different orientations: (1) where the entire cross-sectional surface of the kernel was in the cutting plane, (2) where the lengthwise axis of the kernel was in the cutting plane, and (3) where the lengthwise axis of the kernel was at a 45 degree angle to the cutting plane. All samples were classified correctly indicating that orientation of the grain during cutting did not affect the results of the method.

It is understood that the foregoing detailed description is given merely by way of illustration and that modification and variations may be made within without departing from the spirit and scope of the invention.

Having thus described the invention, I claim:

1. A method for classifying a wheat kernel as hard or soft, comprising:
    (a) cutting a wheat kernel having an aleurone layer and a subaleurone layer and having at least one substantially flat, planar face located below said subaleurone layer, said cutting carried out at a predetermined distance from said face and substantially parallel thereto, to obtain a kernel section having a thickness of about 1.3 to 4.8 microns; and
    (b) classifying said kernel as hard if said section remains intact and classifying said kernel as soft if said section does not remain intact.

2. The method of claim 1 wherein said thickness of said section is about 1.5 to 4.5 microns.

3. The method of claim 1 wherein said thickness of said section is selected from the group consisting of 1.6, 2, 2.5, 3, and 4 microns.

4. The method of claim 1 wherein said face is located at a distance of at least 50 microns below said aleurone layer.

* * * * *